United States Patent [19]

Chiou

[11] Patent Number: 4,772,616
[45] Date of Patent: Sep. 20, 1988

[54] TREATMENT OF OCULAR HYPERTENSION AND GLAUCOMA WITH DOPAMINE ANTAGONISTS

[75] Inventor: George C. Y. Chiou, College Station, Tex.

[73] Assignee: The Texas A & M University System, College Station, Tex.

[21] Appl. No.: 94,968

[22] Filed: Sep. 9, 1987

Related U.S. Application Data

[60] Continuation of Ser. No. 015,540, Feb. 13, 1987, abandoned, which is a division of Ser. No. 818,653, Jan. 13, 1986, abandoned, which is a continuation-in-part of Ser. No. 477,179, Mar. 21, 1983, Pat. No. 4,565,821.

[51] Int. Cl.$^4$ .......................................... A61K 31/445
[52] U.S. Cl. .................................... 514/322; 514/913
[58] Field of Search ............................. 514/322, 913

[56] References Cited

U.S. PATENT DOCUMENTS

| | | | |
|---|---|---|---|
| 4,195,085 | 3/1980 | Stone | 424/248.51 |
| 4,501,749 | 2/1985 | Clineschmidt | 514/320 |
| 4,565,821 | 1/1986 | Chiou | 514/327 |
| 4,657,925 | 4/1987 | Horn | 514/357 |
| 4,657,929 | 4/1987 | Ince et al. | 514/524 |

OTHER PUBLICATIONS

Chem. Abst. 82: 93297(h)—Tuck.
Chem. Abst. 87: 3625(q)—Tso et al.
Chem. Abst. 88: 32029(z)—Scatton et al.
Chem. Abst. 89: 12149(f)—Lapinet et al.
Chem. Abst. 93: 143069(k)—Magnistretti et al.
Chem. Abst. 101: 48632(p)—Chiou.
Chem. Abst. 101: 108222(s)—Sears.
Chem. Abst. 68:20812(y) (1968)—Romos et al.
Chem. Abst. 76:121811(t) (1972)—Schmiedeberg et al.
Chem. Abst. 81: 131070(t) (1974)—James et al.
Potter, D. E., Burke, J. A. and Chang, F. W. (1984), Ocular Hypotensive Action of Ergoline Derivatives in Rabbits: Effects of Sympathectomy and Domperidone Pretreatment. Curr. Eye Res. 3, 307-314.
Shannon, Richard P., "The Effect of Dopamine on the Intraocular Pressure and Pupil of the Rabbit Eye," Inv. Ophtalmology, May 1976.
Potter and Rowland, "Adrenergic Drugs and Intraocular Pressure", Gen. Pharmac., vol. 12, pp. 1 to 13, (1981).
Schmiedeberg et al., "The Influence of Drugs Involved in General Anaesthesia and of Antihypertensive Agents on Intraocular and Blood Pressure in the Rabbit", Drugs & Intraocular Pressure (1971).
James, N., "Low Dosage Haloperidol and Induced Anxiety in Normal Volunteers," New Zealand Medical Journal, vol. 78, Sep. 12, 1973.
Ramos, Laone, "Influencia De Tranquilizantes Derivados Da Butirofenona Na Pressao Intraocular Do Coelho", Rev. Fac. Farm Bioquim. S. Paulo 4(2):259–263, jul./dez. 1966.
Textbook of Pharmacology, W. C. Bowman and on J. Rand, 2nd Edition (1980), published by Blackwell Science Publications, Oxford.
Chiou, George, C. Y. Treatment of Ocular Hypertension and Glaucoma with Dopamine Antagonists, Opthalmic Res. 16:129–134 (1984).
Chiou, George, C. Y. and Faye Y. Dopaminergic, Involvement in Intraocular Pressure in the Rabbit Eye, Opthalmic Res. 15:131–135 (1983).
Chiou, George, C. Y., Ocular Hypotensive Actions of Nalperidol, A Dopaminergic Antagonist, Arch. Opthalmol. 102: (Jan. 1984).

Primary Examiner—Douglas W. Robinson

[57] ABSTRACT

Aqueous humor formation and intraocular pressure in mammals having ocular hypertension or glaucoma may be reduced by topically administering to a hypertensive eye an ophthalmologically acceptable amount of certain dopamine antagonists or acid addition salts thereof. A preferred group of dopamine antagonists is the 4-piperidino-4'-fluoro-butyrophenones, especially haloperidol, trifluperidol, and moperone. The phenothiazines are another suitable group of dopamine antagonists. An ophthalmic composition for topically treating glaucoma may comprise an aqueous solution containing 0.01% to 5% by weight of a water-soluble ophthalmologically acceptable acid addition salt of such dopamine antagonist.

6 Claims, 5 Drawing Sheets

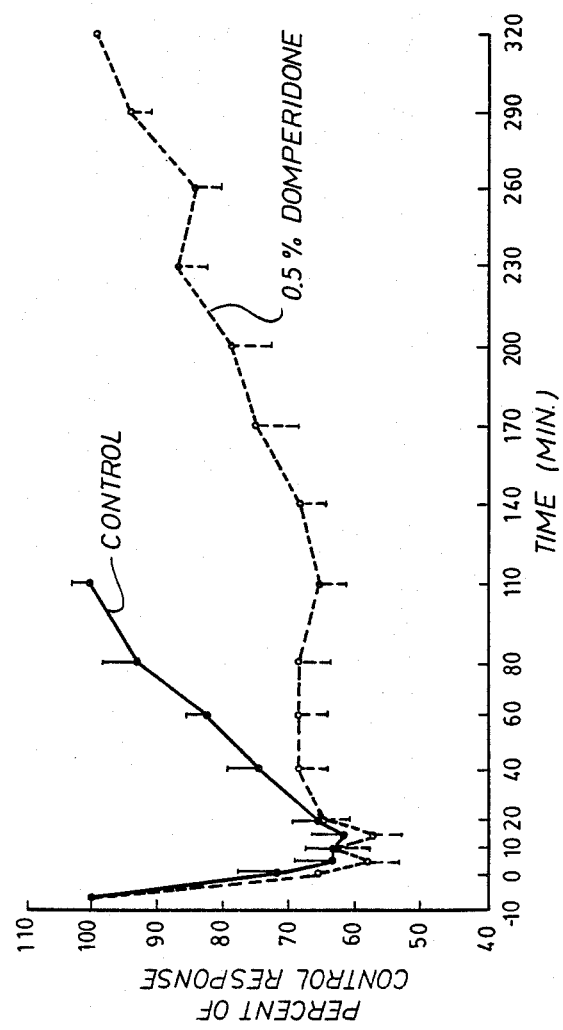

TREATMENT OF OCULAR HYPERTENSION AND GLAUCOMA WITH DOPAMINE ANTAGONISTS

This application is a continuation of prior copending application Ser. No. 15,540, filed Feb. 13, 1987, now abandoned which was a division of prior application Ser. No. 818,653 filed Jan. 13, 1986, now abandoned, which was a continuation-in-part of application Ser. No. 477,179, filed Mar. 21, 1983, now U.S. Pat. No. 4,565,821.

BACKGROUND OF THE INVENTION

This invention relates to ophthalmologically acceptable dopamine antagonists and ophthalmologically acceptable acid addition salts thereof and their use to lower intraocular pressure, especially in the treatment of ocular hypertension and glaucoma.

Glaucoma is an optical neuropathy associated with elevated intraocular pressures which are too high for normal function and result in irreversible loss of visual function. If untreated, glaucoma may eventually lead to blindness. Ocular hypertension, i.e., the condition of elevated intraocular pressure without optic nerve head damage or characterstic glaucomatous visual field defects, is now believed by many ophthalmologists to represent the earliest phase of glaucoma.

Many of the drugs formerly used to treat glaucoma proved not entirely satisfactory. Indeed, few advances have been made in the treatment of glaucoma since pilocarpine and timolol were introduced. Timolol, 1-tert-butyl-amino -3-[(4-morpholino-1,2,5-thiadiazol-3-yl) oxy]-2-propanol, is a $\beta$-adrenergic blocking agent which has been found to be effective in reducing intraocular pressure without many of the undesirable side effects associated with pilocarpine. In addition, timolol possesses advantages over many other $\beta$-adrenergic blocking agents, including a lack of local anesthetic action, long duration of activity, and minimal tolerance. Nevertheless, timolol must be used with caution in those patients having elevated intraocular pressure who also suffer from bronchial asthma, sinus bradycardia with greater than first degree block, cardiogenic shock, right ventricular failure secondary to pulmonary hypertension, or congestive heart failure. Further, the concomitant use of timolol with adrenergic augmenting cyclopropane-like drugs must be carefully monitored. These precautions are necessary because even when administered topically to the eye, timolol is sufficiently active that a small portion is absorbed into the systemic circulation where it can affect other systems.

The limitations inherent in the use of timolol are indicative of the need for an alternative form of glaucoma therapy. A very recent approach to improved glaucoma therapy is that disclosed in U.S. Pat. No. 4,521,414 entitled "Ophthalmic Compositions and Their Use for Treating Elevated Intraocular Pressure and Glaucoma. " Prior to the invention disclosed in the cited application, timolol had been used only in the form of the isomer having the S configuration (L-timolol) or a racemic mixture. The cited application discloses the use of the R stereoisomeric form of timolol (D-timolol) to obtain an intraocular pressure reducing response substantially equivalent to that of the S isomer, but without the undesirable activity in extraocular systems that result from the use of the S isomer.

SUMMARY OF THE INVENTION

According to the invention of the present application, there is provided a whole new class of drugs for glaucoma treatment comprising ophthalmologically acceptable dopamine antagonists and acid addition salts thereof, especially dopamine antagonists of the butyrophenone type. Because these dopamine antagonists do not stimulate cholinergic systems as does pilocarpine or block $\beta$-adrenergic receptors as does timolol, they do not produce the side effects associated with pilocarpine or L-timolol. Thus the present invention provides a means for effectively reducing intraocular pressure in those patients who have a history of asthma or congestive heart disease or for whom timolol or pilocarpine are either contraindicated or necessarily prescribed with caution.

In particular, the present invention relates to the use of certain ophthalmologically acceptable dopamine antagonists, and ophthalmologically acceptable acid addition salts thereof, for reducing aqueous humor formation and intraocular pressure in mammals having ocular hypertension or glaucoma. Throughout this application, "dopamine antagonist" is used in its usual sense to mean a drug which interacts reversibly with a set of dopamine receptors to form an antagonist-receptor complex, thereby producing a dopaminergic blocking action.

A preferred group of dopamine antagonists for this invention comprises neuroleptic drugs of the butyrophenone type which bind dopamine receptors relatively specifically. Throughout this application, "butyrophenone" is used to refer to that group of butyrophenones having the following structural moiety in common:

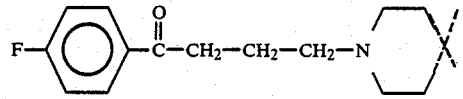

Within the class of butyrophenones is a preferred group of compounds having the structural formula

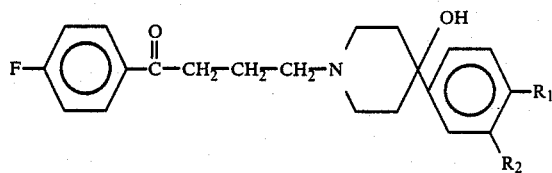

with $R_1$ selected from the group consisting of hydrogen, alkyl, halogen, and halogenated alkyl and $R_2$ selected from the group consisting of hydrogen, alkyl, halogen, and halogenated alkyl.

Specific butyrophenones that have been found to reduce significantly aqueous humor formation and intraocular pressure include haloperidol, trifluperidol, moperone, clofluperol, floropipamide, and lenperone. Of this group of butyrophenones, moperone, trifluperidol, and especially haloperidol, have been found to be particularly effective and more potent than pilocarpine and timolol in lowering intraocular pressure.

Other dopamine antagonists suitable for use in this invention include phenothiazines and domperidone.

In accordance with the method of the present invention, certain dopamine antagonists or acid addition salts thereof are administered in ophthalmologically acceptable amounts that are effective for lowering intraocular pressure. This administration is preferably in the form of an ophthalmic pharmaceutical composition adapted for topical administration to the eye, such as a solution, ointment, or solid insert.

The ophthalmic composition of this invention comprises an ophthalmologically acceptable amount, effective for lowering intraocular pressure, of a suitable dopamine antagonist and a pharmaceutical ophthalmic carrier. In the inventive composition, the selected dopamine antagonist is preferably in the form of a water-soluble ophthalmologically acceptable acid addition salt. A 0.01% to 5% by weight solution of the acid addition salt, and particularly a 0.125% to 0.5% by weight solution, is used to achieve effective reduction of intraocular pressure. Higher dosages as, for example, about 10%, or lower dosages, may be employed provided the dose is ophthalmologically acceptable and effective. Generally, in man, the dose must be patient adjusted to employ the minimal dose that reduces intraocular pressure to an acceptable level. A pharmaceutical unit dosage for the topical treatment of glaucoma comprises generally about 0.005 mgs. to about 2.5 mgs., and preferably about 0.0625 mgs. to about 0.25 mgs., of an ophthalmologically acceptable acid addition salt of a suitable dopamine antagonist in an isotonic aqueous solution.

The more important features of this invention have thus been summarized rather broadly in order that the detailed description thereof that follows may be better understood, and in order that the contribution to the art may be better appreciated. There are, of course, additional features of the invention that will be described hereinafter and which will also form the subject of the claims appended hereto.

BRIEF DESCRIPTION OF THE DRAWINGS

FIG. 9 depicts the time course of percentage change of intraocular pressure (IOP) recovery in rabbits after the administration of ocular hypotensive agents, in the same manner as FIG. 1, except that the effect of a 0.5 wt % aqueous solution of domperidone is compared to the control. Each point is a mean of 6 values.

DETAILED DESCRIPTION OF THE INVENTION

Figure 1:
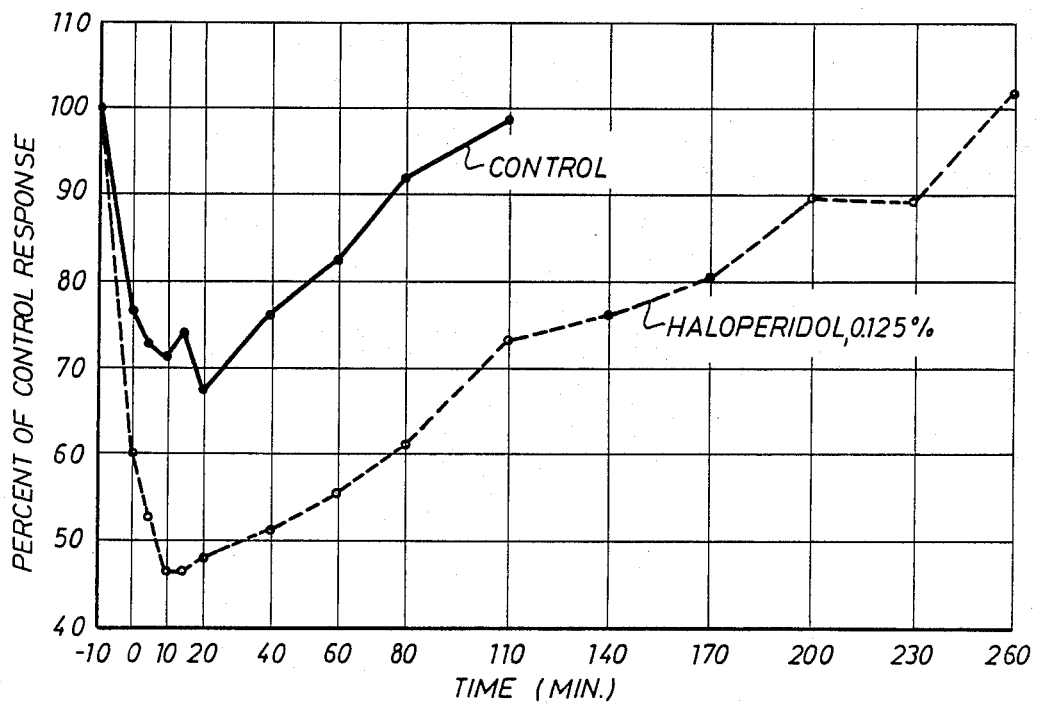
FIG. 1 depicts the time course of percentage change of intraocular pressure (IOP) recovery in rabbits after the administration of ocular hypotensive agents. The control curve represents the effect on IOP of ear vein infusion of a hypertonic saline solution, against which the effect of eye application of a 0.125 wt % aqueous solution of haloperidol is compared. Each point is a mean of 4 values.

The invention as hereinabove stated provides an ophthalmologically active anti-hypertensive agent for the eye, both animal and human, which does not induce undesirable effects on extraocular tissues. Accordingly, certain ophthalmologically acceptable dopamine antagonists and ophthalmologically acceptable acid addition salts thereof provide an effective means for the treatment of ocular hypertension and glaucoma.

The preferred dopamine antagonists for use in this invention are neuroleptic drugs of the butyrophenone type which bind dopamine receptors relatively specifically. Within the class of butyrophenones are specifically preferred compounds which may be characterized as having the general structural formula:

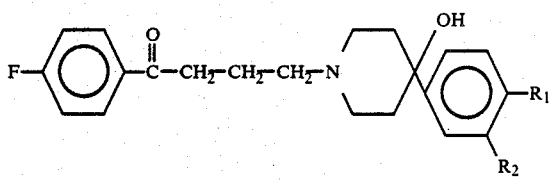

wherein $R_1$ is selected from the group consisting of hydrogen, alkyl, halogen, and halogenated alkyl and $R_2$ is selected from the group consisting of hydrogen, alkyl, halogen, and halogenated alkyl.

The preferred butyrophenone is 4-[4-(p-chlorophenyl)-4-hydroxypiperidino]-4'-fluorobutyrophenone (haloperidol) having the structural formula:

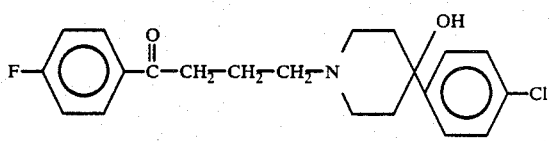

Although haloperidol is used clinically as an antipsychotic drug and produces extrapyramidal side effects, the dosages used in this invention for glaucoma therapy are only 2.2% to 6.5% of the anti-psychotic dosages. Additionally, in general, not more than 10% of all topically instilled drugs are absorbed systemically. Therefore, less than 0.2% to 0.65% of an anti-psychotic dosage level of haloperidol would potentially be absorbed as a result of this glaucoma therapy. Consequently, dopamine blocking side effects are not believed to be significant.

Other suitable dopamine antagonists of the butyrophenone type include the following:

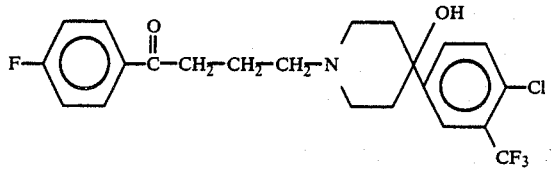

4-[4-(m-trifluoromethyl-p-chlorophenyl)-4-hydroxypiperidino)-4'-fluorobutyrophenone
clofluperol

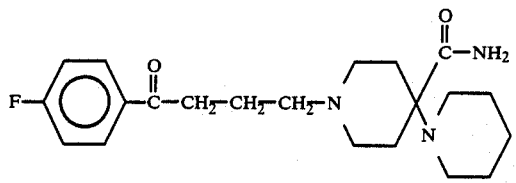

4-[4-(piperidyl)-4-carbamyl]-4'-fluorobutyrophenone
floropipamide

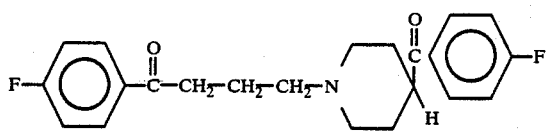

4-(p-fluorobenzoyl-piperidino)-4'fluorobutyrophenone
lenperone

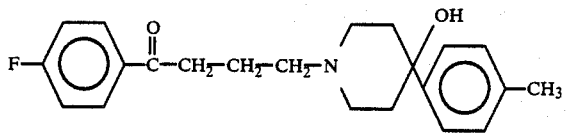

4-[4-(p-methylphenyl)-4-hydroxypiperidino-4'-fluorobutyrophenone
moperone

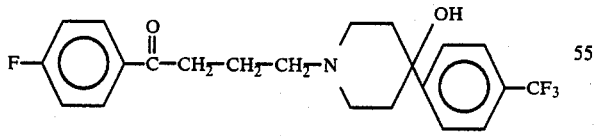

4-[4-(p-trifluoromethylphenyl)-4-hydroxypiperidino]-4'-fluorobutyrophenone
trifluperidol All of the above specifically named butyrophenones are readily available compounds for which methods of synthesizing are well known. Methods for synthesizing butyrophenones are reported in the literature. Janssen et al., *J. Med. Pharm. Chem.* 1:281 (1959); British Pat. No. 881,893 to Janssen (1961); British Pat. No. 895,309 to Janssen (1962); Belgian Pat. No. 610,830 to Janssen (1962).

The butyrophenones described above are particularly effective in reducing aqueous humor formation and intraocular pressure in both animals and humans. Additionally, while clofluperol, floropipamide and lenperone are at least equipotent to timolol to lower intraocular pressure, haloperidol, moperone, and trifluperidol have exhibited more potency than timolol. (See FIGS. 1-5). The action mechanism of haloperidol was found to provide an initial increase in aqueous humor outflow, followed by a decrease in aqueous humor formation. (See FIG. 6). This is a more efficient mechanism to reduce intraocular pressure as compared with pilocarpine, which increases aqueous humor outflow without affecting aqueous humor formation, or timolol, which decreases aqueous humor formation without changing aqueous humor outflow. Furthermore, as the dopamine antagonists of the present invention do not stimulate the cholinergic system as does pilocarpine or block β-adrenergic receptors as does timolol, they do not produce the side effects associated with pilocarpine and timolol.

Another dopamine antagonist suitable for use in this invention is domperidone. Domperidone has the following structural formula:

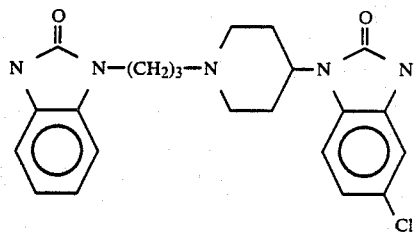

Domperidone is a readily available compound for which methods for synthesizing are well known. Methods for synthesizing domperidone are reported in the literature. Reyntiens, A. J., et al., Arzneit, Forsch. *Drug Esp.* 28:1194-1196 (1978). Domperidone is also available from Stewart Pharmaceuticals, division of ICI Americas, Inc., Wilmington, Del. 19897.

Phenothiazines are another group of dopamine antagonists for use in this invention. Phenothiazines useful in the invention have the following general structural formula:

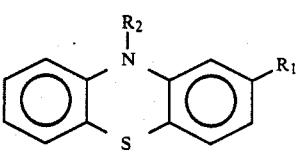

wherein $R_1$ is selected from the group consisting of hydrogen, alkyl, halogen, halogenated alkyl, and $R_2$ is selected from the group consisting of hydrogen, halogen, and halogenated alkyl.

Suitable dopamine antagonists of the phenothiazine type include the following:

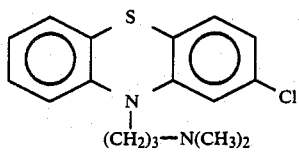

2-chloro-10-(3-dimethylaminopropyl)-phenothiazine
chloropromazine

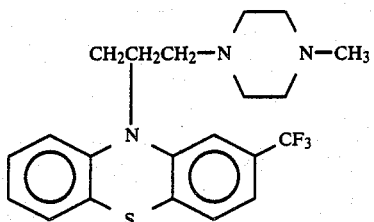

10-[3-(4-methylpiperazine-1-yl)propyl]-2-trifluoromethyl-
phenothiazine
trifluoroperazine The above specifically named phenothiazines are readily available compounds for which methods for synthesizing are well known. Methods for synthesizing phenothiazines are reported in the literature. Charpentier, et al., *Compt. Rend.* 235,59 (1952); U.S. Pat. No. 2,645,640 to Charpentier; Craig, et al., *J. Organic Chem.* 22:709 (1957); British Pat. No. 813,861 (1959); British Pat. No. 829,246 (1960).

Suitable dopamine antagonists are preferably administered in the form of an ophthalmic pharmaceutical composition adapted for topical administration to the eye, such as a solution, solid insert, and the like. The inventive ophthalmic composition comprises an ophthalmologically acceptable amount, effective for reducing intraocular pressure, of a suitable dopamine antagonist compound and a pharmaceutical ophthalmic carrier. In the inventive composition, the selected dopamine antagonist compound is preferably in the form of an ophthalmologically acceptable acid addition salt of the dopamine antagonist.

In the cat and rabbit, a 0.125% to 0.5% by weight solution of the selected dopamine antagonist in an acidic buffer solution (pH4.0 to 6.0) was found effective in lowering intraocular pressure. For other species of animal and man, the dose must be adjusted accordingly. Generally, in man, the dose must be patient adjusted to employ the minimal dose that reduces intraocular pressure to an acceptable level. In general, formulations of this invention may contain from 0.01% to 5% by weight, and especially 0.125% to 0.5% by weight of the dopamine antagonist or its acid addition salt. Higher dosages, as for example, about 10% or lower dosages may be employed, provided the dose is effective in lowering intraocular pressure. As a pharmaceutical unit dosage, between 0.005 to 2.5 mgs., and preferably 0.0625 to 0.25 mgs., of the medicament is generally applied to the human eye.

In addition to the preparations disclosed herein, a pharmaceutical preparation to contain a suitable dopamine antagonist may be prepared by methods as described by Chiou & Watanbe, "Drug Delivery to the Eye," *Pharmac. Ther.*, 17:269-278 (1982), which is hereby incorporated by reference.

The pharmaceutical preparation which contains the compound of this invention may be conveniently admixed with a non-toxic pharmaceutical organic carrier, or with a non-toxic pharmaceutical inorganic carrier. Pharmaceutically acceptable carriers may include water, water mixture of lower alkanols, vegetable oils, polyalkylene glycols, petroleum based jelly, ethyl cellulose, ethyl oleate, carboxymethyl cellulose, polyvinylpyrrolidone, isopropyl myristate, and other conveniently utilized acceptable carriers.

The pharmaceutical solutions may also contain non-toxic substances such as buffers, emulsifiers, wetting agents, and the like. Pharmaceutically acceptable buffers include phosphate, borate, acetate, and glucuronate buffers. It should be noted, however, that the major disadvantage of using ophthalmic solutions is the short duration of drug action. This can be remedied, at least in part by increasing the viscosity of the vehicle with the addition of synthetic compounds such as polyethylene glycols, polyvinyl alcohol, hydroxypropylmethylcellulose, polyvinylpyrrolidone, and the like. Although natural substances such as acacia, tragacanth, and gelatin, are also used, they tend to have high refractive indexes, enhance growth of micro-organisms and are chemically unstable. Consequently, synthetic compounds are preferred.

While the ophthalmic solutions may be entirely satisfactory for many patients, others may prefer a solid medicament that is topically applied to the eye, for example, a solid dosage form that is suitable for insertion into the eye. The inserts are placed in the upper cul-de-sac or, less frequently, in the lower conjunctival sac. Inserts can be made of biologically soluble materials (soluble inserts) which dissolve in lacrimal fluid or disintegrate while releasing the drug. Ocuserts, on the other hand, are insoluble inserts which have to be replaced approximately once a week. Water soluble, non-toxic polymers are used to make the inserts. Suitable polymers which may be utilized for making inserts include cellulose derivatives, such as methylcellulose (cellulose methyl ether), carboxymethylcellulose (CMC, CM cellulose), hydroxyethylcellulose (cellocize), hydroxypropylcellulose, and hydroxypropyl methylcellulose (methylcellulose, propylene glycol ether); acrylates, such as polyacrylic acid salts, ethyl acrylates, and polyacrylamides; polyvinyl derivatives, such as polyvinyl alcohol (PVA; PVOH), polyvinylpyrrolidone (PVP), and polyvinyl methyl ether (PVM); natural products such as gelatin, alginates, pectins, tragacanth, karaya gum, carrageenan, agar, and arabic gum; starch derivatives such as starch acetate, hydroxyethyl starch ethers, and hydroxypropyl starch; as well as polyethylene oxide and xanthan gum, and mixtures of said polymers. The molecular weight of these polymers is not critical and may vary from 10,000 to 1,000,000 or greater.

The insert is readily prepared by dissolving the pharmaceutical preparation of this invention and the polymer in a solvent and the solution evaporated to form a thin film of the polymer, which is then subdivided into the form of a square, rectangle, oval, circle, doughnut, semicircle, quarter moon shape, and the like. Alternatively, the pharmaceutical preparation and the polymer can be warmed and molded to form a thin film of the aforementioned forms.

The inserts can also contain plasticizers (at least 5% up to 40% by weight of the inserts) which are completely soluble in lacrimal fluids. Plasticizers suitable for use include polyethylene glycol (PEG, polyoxyethylene, polyglycol, polyether glycol), propylene glycol (dihydroxypropane, methylene glycol, methyl glycol), glycerine, trimethylolpropane (hexaglycerol), di and tri propylene glycol, hydroxypropyl sucrose, and water.

Suitable buffering agents that are used to prepare inserts include alkali and alkali earth carbonates, acetates, phosphates, bicarbonates, citrates, borates, and the like. The pH of the system is best adjusted to between pH 7 to 8.

The dopamine antagonists of the present invention have been studied with respect to their ability to reduce aqueous humor formation and intraocular pressure in rabbits and cats. The studies indicate that the compounds are effective in reducing aqueous humor formation and intraocular pressure subsequent to topical and intracameral application.

EXAMPLE 1

Albino rabbits of either sex, weighing 2.25–2.5 kg were used for this intraocular pressure (IOP) recovery model experiment. Hypertonic saline (20% NaCl) was infused into the ear vein at a rate of 1 ml/min. for 10 minutes. The IOP was determined with Mackay-Marg electronic applanation tonometer (Berkeley Bio-Engineering, San Leandro, Calif.) at 0, 5, 10, 15, 20, 40, 60, 80, and every 30 minutes thereafter. The IOP decreased abruptly right after the infusion of hypertonic saline and recovered to normal in approximately 80–110 minutes. Identical experiments were repeated with the same group of animals one week later, wherein addition to the hypertonic saline infusion, haloperidol was instilled into the eyes in the form of 50 μl of an aqueous solution of 0.125 wt % haloperidol. The shift of the IOP recovery curve relative to the control curve, as shown in FIG. 1, indicates the ocular hypotensive action of 0.125 wt % haloperidol.

EXAMPLE 2

Figure 2:
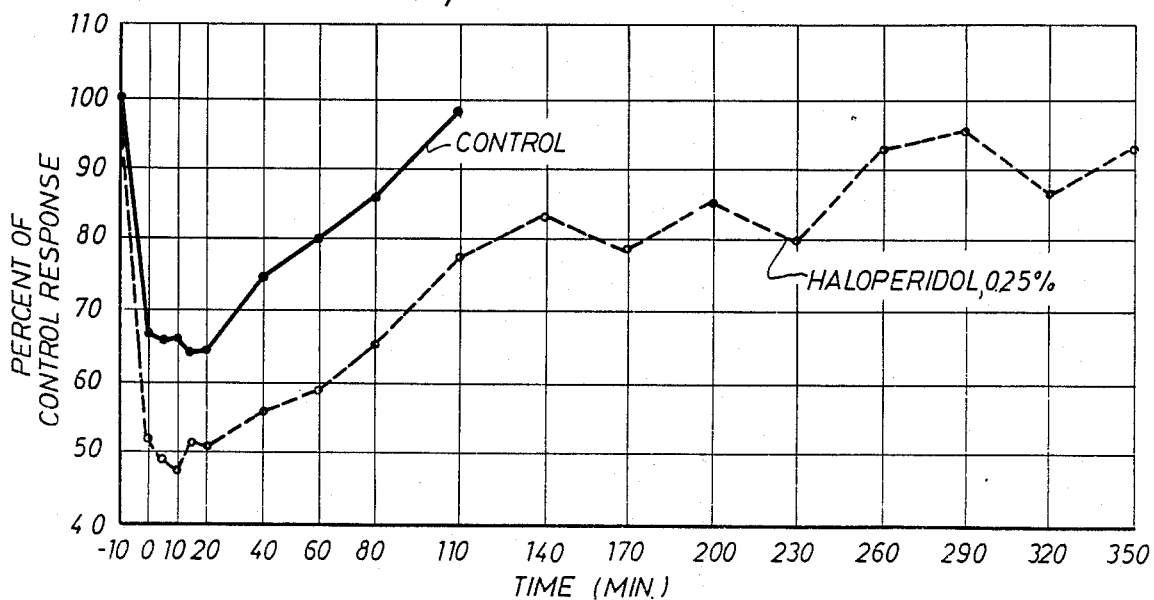
FIG. 2 depicts the time course of percentage change of intraocular pressure (IOP) recovery in rabbits after the administration of ocular hypotensive agents, in the same manner as FIG. 1, except that the effect of a 0.25 wt % aqueous solution of haloperidol is compared to the control. Each point is a mean of 6 values.

The procedure performed in Example 1 was carried out in the same manner, except that an aqueous solution of 0.25 wt % haloperidol was employed. The shift of the IOP recovery curve relative to the control curve, as shown in FIG. 2, indicates the ocular hypotensive action of 0.25 wt % haloperidol.

EXAMPLE 3

Figure 3:
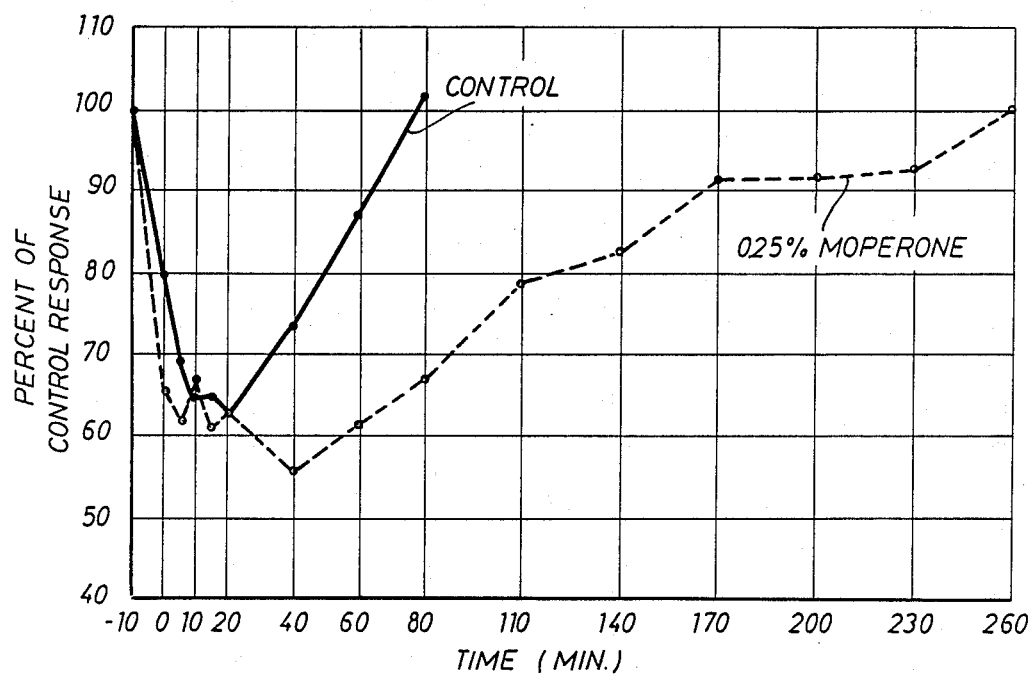
FIG. 3 depicts the time course of percentage change of intraocular pressure (IOP) recovery in rabbits after the administration of ocular hypotensive agents, in the same manner as FIG. 1, except that the effect of a 0.25 wt % aqueous solution of moperone is compared to the control. Each point is a mean of 4 values.

The procedure performed in Example 1 was carried out in the same manner, except that an aqueous solution of 0.25 wt % moperone was used. The shift of the IOP recovery curve relative to the control curve, as shown in FIG. 3, indicates the ocular hypotensive action of 0.25 wt % moperone.

EXAMPLE 4

Figure 4:
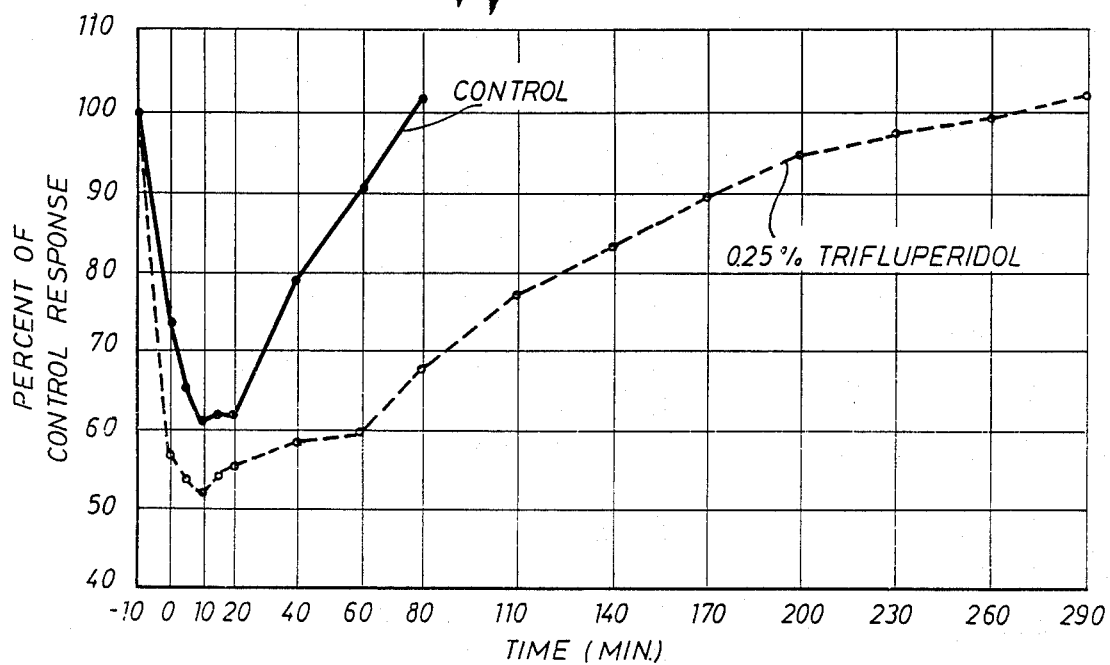
FIG. 4 depicts the time course of percentage change of intraocular pressure (IOP) recovery in rabbits after the administration of ocular hypotensive agents, in the same manner as FIG. 1, except that the effect of a 0.25 wt % aqueous solution of trifluperidol is compared to the control. Each point is a mean of 4 values.

The procedure performed in Example 1 was carried out in the same manner, except that an aqueous solution of 0.25 wt % trifluperidol was used. The shift of the IOP recovery curve relative to the control curve, as shown in FIG. 4, indicates the ocular hypotensive action of 0.25 wt % trifluperidol.

EXAMPLE 5

Figure 5:
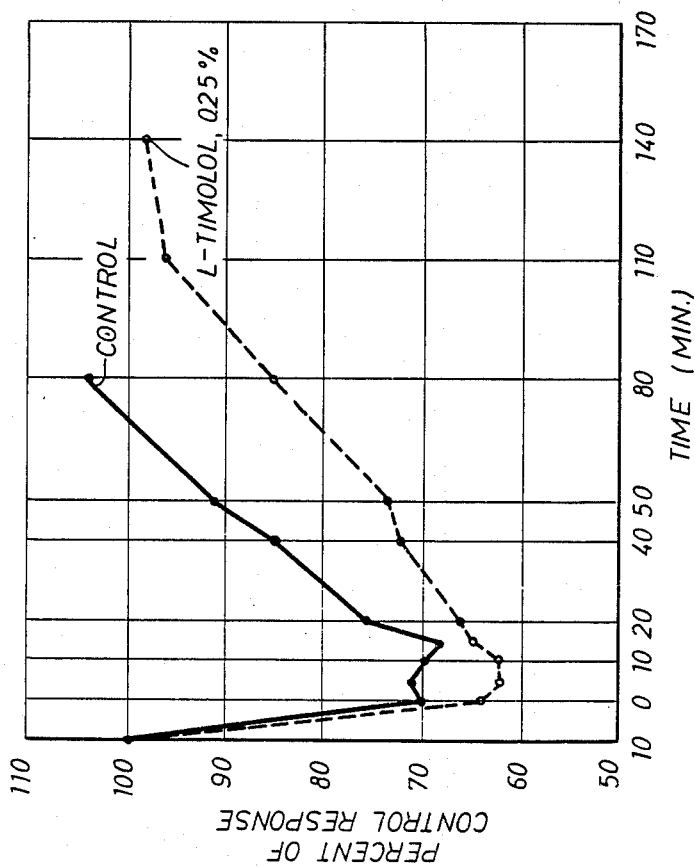
FIG. 5 depicts the time course of percentage change of intraocular pressure (IOP) recovery in rabbits after the administration of ocular hypotensive agents, in the same manner as FIG. 1, except that the effect of a 0.25 wt % aqueous solution of timolol is compared to the control. Each point is a mean of 6 values.

The procedure performed in Example 1 was carried out in the same manner, except that an aqueous solution of 0.25 wt % L-timolol was used. The shift of the IOP recovery curve relative to the control curve, as shown in FIG. 5, indicates the ocular hypotensive action of 0.25 wt % L-timolol.

EXAMPLE 6

The procedure performed in Example 1 was carried out in the same manner, except that an aqueous solution of 0.25 wt % clofluperol was used. The IOP recovery was determined to be generally equivalent to that of L-timolol.

EXAMPLE 7

The procedure performed in Example 1 was carried out in the same manner, except that an aqueous solution of 0.25 wt % floropipamide was used. The IOP recovery was determined to be generally equivalent to that of L-timolol.

EXAMPLE 8

The procedure performed in Example 1 was carried out in the same manner, except that an aqueous solution of 0.25 wt % lenperone was used. The IOP recovery was determined to be generally equivalent to that of L-timolol.

EXAMPLE 9

The cat eye model was used for the study of haloperidol actions in aqueous humor (AH) dynamics. Briefly, cats of either sex weighing 2.5–4.0 kg were anesthetized with 30 mg/kg of pentobarbital sodium. Systemic blood pressure was monitored through cannulation at the femoral artery and additional pentobarbital was injected via femoral vein. Three needles were put into each eye. The first one was placed in the anterior chamber for the monitoring of IOP. The second one was placed at the posterior chamber for the infusion of AH-like solution containing 0.01% of blue dextran (NaCl, 137; KCl, 4.7; CaCl$_2$, 1.53; MgCl$_2$, 0.67; Na$_2$HPO$_4$, 0.11 and dextrose, 5.56 mM). The rate of the infusion was adjusted to 38 μl/min. The third one was placed in the anterior chamber to serve as an overflow outlet. The overflown solution passed through a microspectrophotometric cell (ISCO, UA-5, Lincoln, Nebr.) for the detection of changes of blue dextran concentration and through a drop counter (ISCO, Model 328) for the recording of overflow rate.

Haloperidol (50 μl of 0.5% eye drops) was instilled to the eyes when the blue dextran tracings were stabilized (in about 2 hrs. after the initiation of the infusion). The rates of AH formation ($r_f$) and outflow ($r_o$) were calculated as follows:

$$r_f = r_i(C_i/C_o - 1)$$

and $$r_o = r_i + r_f - r_{overflow}$$

where $C_i$=blue dextran concentration in infusate, $C_o$=blue dextran concentration in overflown AH-like solution, and $r_i$=rate of infusion at 38 μl/min.

Figure 6:
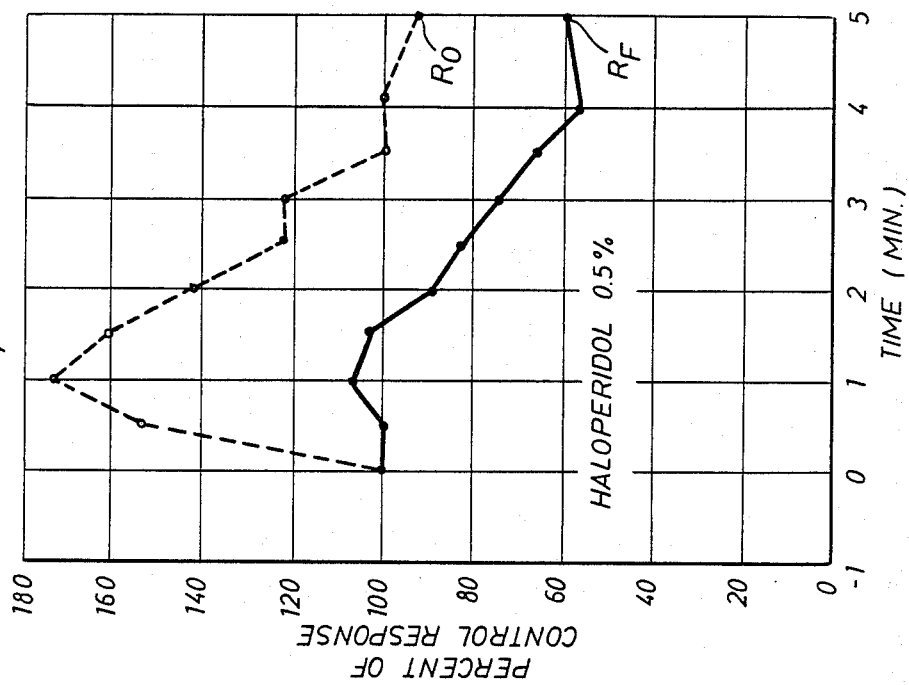
FIG. 6 depicts the time course of percentage change of aqueous humor (AH) dynamics in cats after the administration of 0.5 wt % haloperidol where $r_o$=rate of AH outflow; $r_f$=rate of AH formation. Each point is a mean of 4 values.

As shown in FIG. 6, haloperidol initially caused an increase in AH outflow, which was followed by a decrease in AH formation.

EXAMPLE 10

Figure 7:
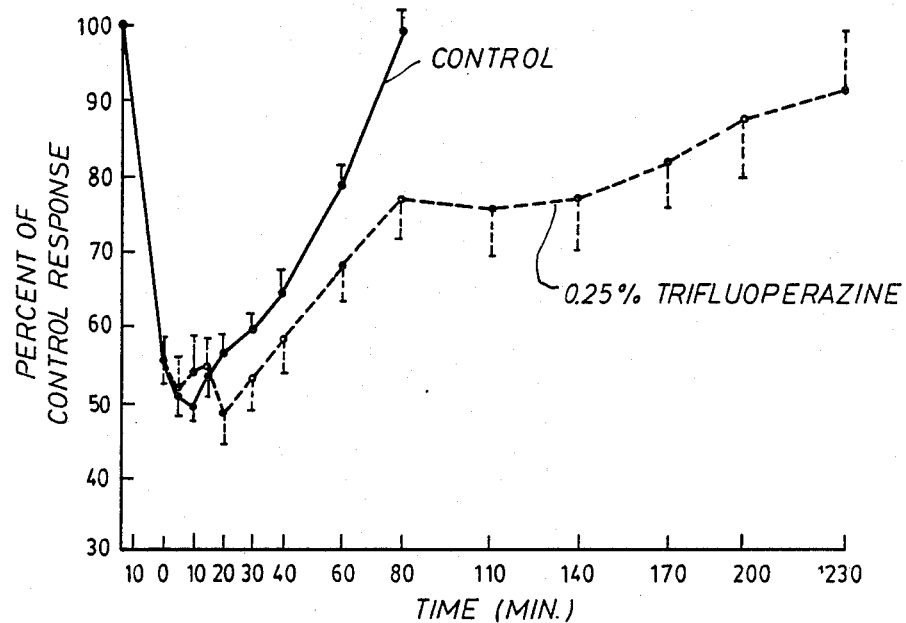
FIG. 7 depicts the time course of percentage change of intraocular pressure (IOP) recovery in rabbits after the administration of ocular hypotensive agents, in the same manner as FIG. 1, except that the effect of a 0.25 wt % aqueous solution of trifluoperazine is compared to the control. Each point is a mean of 6 values.

The procedure performed in Example 1 was carried out in the same manner with the following exceptions: (a) an Alcon electronic applanation tonometer (Alcon Laboratories, Inc., Ft. Worth, Tex.) was used to determine IOP; and (b) an aqueous solution of 0.25 wt % trifluoperazine was used. The shift of the IOP recovery curve relative to the control curve as shown in FIG. 7, indicates the ocular hypotensive action of 0.25 wt % trifluoperazine.

EXAMPLE 11

Figure 8:
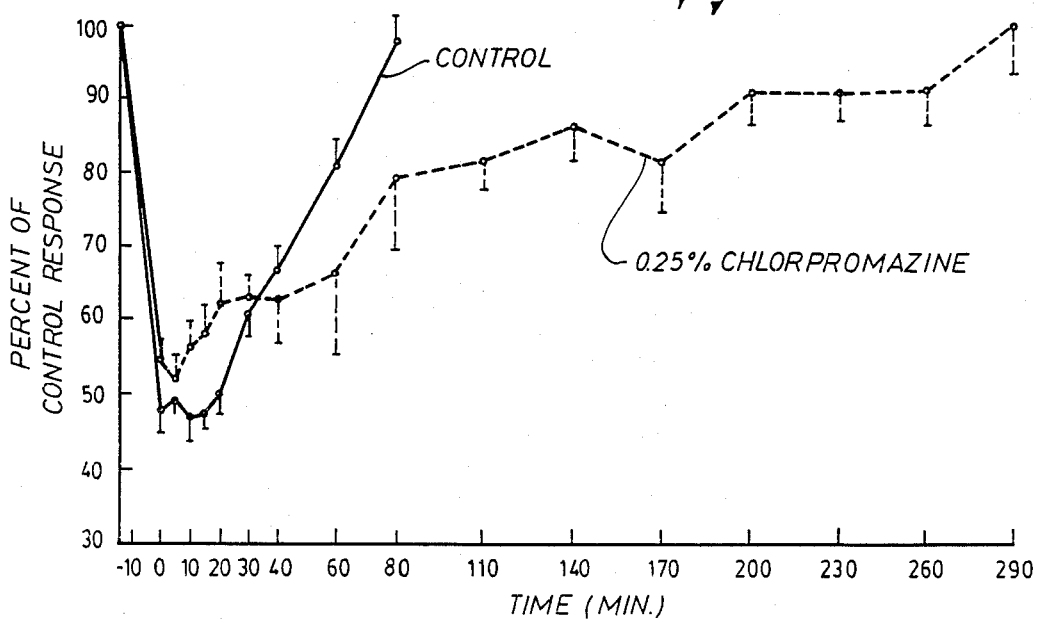
FIG. 8 depicts the time course of percentage change of intraocular pressure (IOP) recovery in rabbits after the administration of ocular hypotensive agents, in the same manner as FIG. 1, except that the effect of a 0.25 wt % aqueous solution of chlorpromazine is compared to the control. Each point is a mean of 6 values.

The procedure performed in Example 10 was carried out in the same manner, except that an aqueous solution of 0.25 wt % chlorpromazine was used. The shift of IOP recovery curve relative to the control curve, as shown in FIG. 8, indicates the ocular hypotensive action of 0.25 wt % chlorpromazine.

EXAMPLE 12

The procedure performed in Example 10 was carried out in the same manner, except that an aqueous solution of 0.5 wt % domperidone was used. The shift of the IOP recovery curve relative to the control curve, as shown in FIG. 9, indicates the ocular hypotensive action of 0.5 wt % domperidone.

The results depicted in FIGS. 1–5 and 7–9 are summarized below in Table A, which lists the drug doses in order of increasing potency for inhibition of IOP recovery.

TABLE A

Potencies of Dopamine Antagonists on IOP Recovery in Rabbit

| Drug Dose | Number of Test Rabbits | Difference in Time Delay for IOP Recovery Relative to Control (min) | Max Reduction of IOP* (% of base control IOP) |
| --- | --- | --- | --- |
| 20% Saline alone | 38 | — | 65 ± 1 |
| Timolol 0.25% | 6 | 60 | 62 ± 4 |
| Clofluperol 0.125% | 4 | 60 | 59 ± 2 |
| Floropipamide 0.25% | 6 | 60 | 60 ± 3 |
| Lenperone 0.25% | 4 | 60 | 61 ± 2 |
| Moperone 0.25% | 4 | 180 | 55 ± 1 |
| Trifluperidol 0.25% | 4 | 180 | 51 ± 2 |
| Haloperidol 0.125% | 4 | 180 | 45 ± 2 |
| Haloperidol 0.25% | 6 | 270 | 46 ± 2 |
| Domperidone 0.5% | 6 | 210 | 56 ± 4 |
| Chlorpromazine 0.25% | 6 | 120 | 52 ± 3 |
| Trifluoperazine 0.25% | 6 | 150 | 49 ± 4 |

*The 100% control IOP of rabbits was 20.2 ± 1.3 mm Hg.

The foregoing description has been directed to particular embodiments of the invention in accordance with the requirements of the Patent Statutes for the purpose of illustration and explanation. It will be apparent, however, to those skilled in the art that many modifications and changes will be possible without departing from the spirit and scope of the invention. It is intended that the folowing claims be interpreted to embrace all such modifications and changes.

What is claimed is:

1. A method of reducing aqueous humor formation and intracular pressure in mammals having elevated intraocular pressure which comprises topically administering to the eye an effective amount for lowering intraocular pressure, of domperidone or an ophthalmologically acceptable acid addition salt thereof.

2. The method according to claim 1, wherein said compound is in the form of a water-soluble ophthalmologically acceptable acid addition salt and is applied topically in an aqueous solution containing between about 0.01% and about 5% by weight of said compound.

3. The method of claim 2 wherein said compound is applied topically in an aqueous solution containing between about 0.125% and about 0.5% by weight of said compound.

4. The method according to claim 1, wherein said compound is topically applied in the form of an ointment.

5. The method according to claim 1 comprising placing in the eye a polymeric ocular insert which contains domperidone, said compound being diffusible from said insert at a rate sufficient to provide an effective intraocular pressure lowering dose thereof to the eye when said insert is in contact therewith.

6. The method of claim 5 wherein the polymer comprising the polymeric ocular insert is hydroxypropyl cellulose.

* * * * *